United States Patent [19]

Desmolin

[11] Patent Number: 5,344,657
[45] Date of Patent: Sep. 6, 1994

[54] MICROBEADS OF DILTIAZEM, A PROCESS FOR THEIR MANUFACTURE AND A SUBSTAINED-RELEASE PHARMACEUTICAL COMPOSITION CONTAINING THEM

[75] Inventor: Henri Desmolin, Merignac, France

[73] Assignee: Elf Sanofi, Paris, France

[21] Appl. No.: 43,592

[22] Filed: Apr. 5, 1993

Related U.S. Application Data

[63] Continuation of Ser. No. 795,247, Nov. 18, 1991, abandoned, which is a continuation of Ser. No. 336,133, Apr. 11, 1989, abandoned.

[30] Foreign Application Priority Data

Apr. 27, 1988 [FR] France ................................ 88 05629

[51] Int. Cl.$^5$ ................................................. A61K 9/54
[52] U.S. Cl. ..................................... 424/458; 424/451; 424/459
[58] Field of Search ......................... 424/458, 451, 459

[56] References Cited

U.S. PATENT DOCUMENTS

| | | | |
|---|---|---|---|
| 4,808,413 | 2/1989 | Joshi et al. | 424/458 |
| 4,894,240 | 1/1990 | Geoghegan et al. | 424/459 |
| 4,917,899 | 4/1990 | Geoghegan et al. | 424/459 |
| 5,149,542 | 9/1992 | Valducci | 424/451 |

FOREIGN PATENT DOCUMENTS

| | | |
|---|---|---|
| 0099109 | 1/1984 | European Pat. Off. . |
| 0149920 | 7/1985 | European Pat. Off. . |
| 0207041 | 12/1986 | European Pat. Off. . |
| 0216743 | 4/1987 | European Pat. Off. . |
| 2091203 | 7/1982 | United Kingdom . |

*Primary Examiner*—Thurman K. Page
*Assistant Examiner*—William E. Benston, Jr.
*Attorney, Agent, or Firm*—Wegner, Cantor, Mueller & Player

[57] ABSTRACT

The microbeads are composed of a core containing the active ingredient and a microporous membrane, insoluble in aqueous medium, consisting of a film-forming polymer, a plasticizer and a filling material.

The membrane has a thickness such that diltiazem is released in vitro at an approximately constant rate for at least 6 hours after a latent period of less than one hour.

The active ingredient can be intimately mixed with the core or included in a polyvinyl pyrrolidone layer coating an inert grain.

The sustained-release microbeads are formed by application to the core of a dispersion of the constituents of the membrane in a solvent and evaporation of the solvent.

The pharmaceutical compositions consist of capsules containing the microbeads. They are administered orally one or twice per day, depending on the dose, for the treatment of angina or hypertension.

18 Claims, No Drawings

MICROBEADS OF DILTIAZEM, A PROCESS FOR THEIR MANUFACTURE AND A SUBSTAINED-RELEASE PHARMACEUTICAL COMPOSITION CONTAINING THEM

This application is a continuation of U.S. application Ser. No. 07/795,247 filed Nov. 18, 1991, now abandoned, which is a continuation of Ser. No. 07/336,133, filed Apr. 11, 1989, abandoned.

The present invention relates to a sustained-release form of diltiazem, a calcium antagonist used in the treatment of angina and hypertension of several years.

It is known that the half-life of this active ingredient is short, of the order of hour hours, and the drug is presently administered in the form of tablets three or four times per day, which is all the more exacting for the patient because his treatment must be continued for prolonged periods. Furthermore, in the case of the administration of this pharmaceutical form, the plasma concentration varies widely between the two doses so that the therapeutic efficacy is not continuous and there exists an increased risk of side effects at peak concentrations.

Consequently, it is desirable to have a pharmaceutical form which gives rise to sustained-release of an approximately constant concentration of this active ingredient so that it is possible to administer the drug only once or twice a day.

Different means are known for the obtention of sustained-release pharmaceutical forms which can be administered orally either in the form of tablets or in the form of microgranules, such as those described in EP-A-0 076 428, EP-A-0 061 217 and EP-A-0 216 743.

Such means must be adapted to each drug since the rate and duration of release of the active ingredient as well as its plasma concentration depend on its physicochemical properties, including its solubility and stability in the gastro-intestinal tract, and on its pharmacokinetic parameters.

Such a form is particularly difficult to prepare for compounds of short half-life, less than 4–5 hours, such as diltiazem, since the duration of its release in vivo from the pharmaceutical form does not exceed the residence time of the drug in the gastro-intestinal tract, i.e. maximally 8 to 10 hours, and then only if release commences immediately on arrival in the stomach.

Furthermore, during this period release is required to be more or less constant although the pH of the surrounding medium changes from 1.5 in the stomach to 6.9 in the jejunum.

One of the objects of the present invention is a sustained-release pharmaceutical composition of diltiazem which, depending on the type of treatment, requires only one or two daily administrations by the oral route. It consists of a capsule of gelatin, starch or other polymer which can be rapidly degraded in the gastric environment, containing a large number of microbeads composed of a core containing the active ingredient surrounded by a microporous membrane, this membrane being composed of a non-water-soluble film-forming polymer, a plasticizer and a filling material; the thickness of the membrane of the microbeads as well as the amount of active ingredient in the core and its size are chosen such that diltiazem is liberated from the microbeads in vitro in artificial dissolution media in which the pH varies from 1.5 to 7, at a substantially constant rate for at least 6 hours, after a latent period of less than one hour.

The core may be constituted of small spheres, produced by extrusion/sphere-formation from a plastic mass based on a polyol such as mannitol or a polymer such as polyglycol, and a water-soluble salt of diltiazem, but a core is preferred which consists of a inert grain composed of excipients, this inert grain being coated with the active ingredient.

The inert grain may be constituted by a sugar, with a hydrocolloid, such as gum arabic, gelatin or starch or a biocompatible polymer such as the micro-crystalline celluloses. alkylcelluloses, carboxymethylcelluloses as well as mixtures of them or other excipients well known to the specialist skilled in the art. A mineral filling material such as talc may be added if required. The inert grain can be prepared in a standard manner in a turbine, or by extrusion/sphere-formation from polymers or by granulation of a molten mass passing through a vibrating nozzle before cooling.

The active ingredient is then bound to the inert grain in one or several successive layers in a turbine or in a fluidized bed either by the spraying of a solution or suspension of the diltiazem salt and a polymeric binder with evaporation of the solvent, or by the spraying of an alcoholic solution of the binder onto the substrate followed by spraying of the diltiazem salt as a powder onto the viscous layer just deposited; the second solution is preferred since the cores thus obtained form less aggregates and are more regular.

Preferably, an appreciable quantity of active ingredient should not be left in the microbeads when, in vivo, they leave the duodanal resorption zone, which corresponds in vitro to the release of at least 60% of the active ingredient from the core within 8 hours, and the concentration of active ingredient in the core is calculated as a function of this.

Usually, for technical reasons, it is preferable that the concentration of active ingredient in the core is 30 to 50% by weight, but in particular in the case of the higher dosage pharmaceutical compositions according to the invention, there may be up to 85% of active ingredient in the core.

It is desirable to have microbeads of a diameter warying between 0.4 and 1.4 mm, so that the number of microbeads introduced into a capsule of acceptable dimensions which can be swallowed by the patient without difficulty, is more than 100 and preferably lies between 200 and 600; thus the dose of the active ingredient and the kinetics of its release will be of an acceptable reproducibility from one capsule to another in spite of the unavoidable heterogeneity of the microbeads due to the manufacturing techniques. Under these conditions the cores will preferably have diameters warying between 0.4 mm and 1.3 mm. In the case in which the active ingredient is bound by a binder to the inert grain from 5 to 20% by weight of binder is used in relation to the weight of the diltiazem salt. Binders which can be used are water-soluble binders well known to the technique, and which are compatible with the diltiazem salt, such as methylcelluloses, water-soluble polyacrylates and polyvinylpyrrolidones. A polyvinylpyrrolidone of molecular mass of approximately 50,000, marketed by GAF (FGR) under the trade name Plasdone, is preferably used.

As diltiazem salt, the standard salt, namely the hydrochloride is usually used but other more or less water-soluble salts may be used, either salts of mineral acids such as the sulfate, or salts of organic acids such as fumarate, oxalate, succinate and similar compounds; the amount of active ingredient in the core and the thickness of the membrane will be defined as a function of the solubility of the salt in aqueous medium.

A fundamental feature of the invention resides in the choice of the properties of the microporous membrane which surrounds the core.

In fact, it has been observed that, in order to obtain a sustained-release pharmaceutical form, having acceptable in vivo kinetics, it is necessary that the in vitro diffusion kinetics of the diltiazem salt from the microbeads in standard artificial dissolution media in which the pH varies from 1.5 to 7 is approximately constant for at least 6 hours and preferably up to 8 hours, and the time necessary to obtain a constant rate of diffusion, i.e. the latent period, is less than one hour.

Under these conditions, capsules containing 120 mg of active ingredient included in microbeads of the invention, administered twice a day to human subjects gives rise, at equilibrium, to a plasma concentration which is always higher than 80 ng/ml, with a peak close to 130 ng/ml which is reached within 6 hours, whereas a standard pharmaceutical composition administered twice a day at the same doses rapidly gives rise to a peak concentration of up to 180 ng/ml with a rapid decrease to 50 ng/ml after 6 hours.

Of the non-water-soluble biocompatible polymers which are stable in vivo and capable of constituting the microporous membrane, mention may be made of the polyacrylates and polymethacrylates of the Eudragit type, the alkylcelluloses including the methylcelluloses of the Tylose type (Hoechst) and the ethylcelluloses such as those marketed by Hercules and the lacquers of natural origin such as the shellac gums. The properties of the last-mentioned are poorly reproducible from cane batch to another and ethylcellulose, the viscosity of which, when measured according to the method of the US National Formulary, lies between 10 and 50 mPa.s, is preferred since it is of reproducible quality and chemically inert.

The polymers must be combined with a plasticizing agent so that the membrane is not brittle, and with a finely divided filling material which may amount to between 35 and 75% by weight of the membrane.

Of the plasticizing agents which may be used, in particular phthalic esters, polyethylenglycols, castor oil and glycerol, castor oil is preferred.

The amount of plasticizing agent introduced depends on the type used. It usually represents 10 to 30% by weight of the film-forming agent.

The presence of a filling material in sufficient amount is fundamental; it reduces the swelling time of the membrane in vivo, hence the latent period, without simultaneously increasing excessively the rate of diffusion of the active ingredient; a low diffusion rate, necessary for a sustained release form, can be obtained by increasing the thickness of a membrane of conventional composition, but the latent period is simultaneously increased.

It is known that in the case of diltiazem, it is of fundamental importance to have a short latent period, in order to avoid bioavailability losses and release of the active ingredient during too short a period before the microbeads leave the gastro-intestinal tract. Nonetheless, in order to reduce this latent period, it is not possible to reduce the thickness of the membrane excessively as this would make it difficult to reproduce its diffusion properties during manufacture; the heterogeneity which would result in the case of the beads thus obtained in the same batch or in successive batches would make it practically impossible to manufacture pharmaceutical compositions, the rate of release of the active ingredient from which is defined and reproducible.

Of the finely divided filling materials which can be used, and which are insoluble in the solvent in which the membrane is applied, mention may be made of talc, silica, metal silicates such as Al and Mg silicates, kaolin, powdered lactose and sucrose, metal oxides such as titanium oxides, or their mixtures. Neutral filling materials such as talc are preferred.

In a preferred embodiment of the invention, the membrane is constituted of 25 to 40% by weight of ethylcellulose, from 5 to 10% by weight of castor oil and from 50 to 70% by weight of talc.

The microporous membrane can be applied by spraying an alcoholic or aqueous-alcoholic dispersion of the film-forming polymer, plasticizing agent and filling material into a turbine or into an air-operated fluidized bed.

In the case of an ethylcellulose-based membrane, its thickness will vary between 15 micrometers and 60 micrometers.

The amount of the composition to be deposited in order to form a membrane of suitable thickness is determined by preliminary tests during which the rate of diffusion of diltiazem in vitro is measured under the standard conditions of the United States Pharmacopea (USP 21. Chap. 711, page 1243; apparatus No. 1) using artificial dissolution media of different pHs varying from 1.5 to 7 and being, for example, 1.5, 4.5 and 7, starting from microbeads containing the selected core and membranes of different thicknesses deposited in successive layers. The thickness of the membrane is then chosen so that an approximately constant rate of diffusion is established within less than one hour and from the measured value of the diffusion rate from the microbeads with this membrane thickness are deduced what must be the dimensional characteristics of the core in order to insure the in vitro release per hour of about 10% of the amount of active ingredient present.

It has in fact been observed that this in vitro rate of release gives plasma concentrations in vivo which are satisfactory for the intended therapeutic use.

The microbeads of the invention are stable; the kinetics of in vitro dissolution do not change during storage as has frequently been observed with this type of pharmaceutical form.

The pharmaceutical compositions according to the invention can be made available in the form of capsules of conventional composition and size containing from 100 to 600, and preferably from 200 to 350, microbeads of the invention such that a unit dose contains from 90 mg to 350 mf of diltiazem. The required number of microbeads are introduced into each capsule; the same microbeads can be used irrespective of the unit dose to be made up but, for extreme doses, it is preferable in particular to select the composition and size of the microbeads such that the number of microbeads per capsule lies between 300 and 350.

These microbeads can be introduced into other pharmaceutical forms: cachets, divisible or indivisible tablets, suppositories and liquid or gelled suspensions.

In what follows, particular embodiments of the invention are described as examples of the microbeads, the process for their preparation and novel sustained-release pharmaceutical compositions of the invention.

The curves of dissolution in artificial media of various pH prepared as described in the U.S.P. have been plotted with an apparatus into which the quantity of microbeads corresponding to the dose of active ingredient have been introduced per liter of medium. The diltiazem hydrochloride released as a function of time is measured by spectrophotometry.

EXAMPLE

In order to prepare about 10 kg of granular substrate, about 2 kg of "seed" obtained by sieving crystallized sucrose through a 0.500 mm mesh sieve and freed of dust by sieving through a 0.200 mm mesh sieve are introduced into a turbine.

An aqueous-alcoholic solution containing sucrose (6 parts) and polyvidone K30 (one part) in a water-ethyl alcohol mixture (50/50—V/V), i.e. about 5 liters for 2.5 kg of sucrose/polyvidone mixture, are sprayed several times.

Between each spraying, dusting is done with a mixture of talc (one part), maize starch (one part) and sucrose (2 parts) until microspheres of about 0.5 to 0.6 mm diameter are obtained. After drying in an incubator at 40° C., the fraction with diameters included between 0.600 mm and 0.300 mm is isolated; it will subsequently be used as the granular substrate.

About 1.5 kg of granular substrate are then introduced into a turbine and its weight is approximately doubled by spraying with a 10% (wt/v) alcoholic solution of polyvidone and dusting between each spraying with diltiazem hydrochloride previously passed through a 0.5 mm mesh sieve until about 2.5 kg of cores are obtained. Drying is performed in an incubator at 40° C.

The content of active ingredient is of the order of 40% by weight. The small cores are removed by means of a 0.6 mm mesh sieve and the cores are reintroduced into a turbine equipped with a spraying device. An alcoholic solution containing about 12% by weight of a mixture of ethyl cellulose (5 parts) and castor oil (one part) is sprayed onto the cores which are dusted with talc between sprayings; the ethylcellulose has a viscosity of from 18 to 24 mPa.s.

When the mass of the beads has increased by 10% a first sample A is taken, then the deposition of the membrane is continued to give a sample B taken after a weight increase of 30%, and a sample C taken after a weight increase of 55%; these three batches are dried in an incubator at 40° C. The kinetics of dissolution for each of them are determined in vitro at pH 1.5, and hence the release per hour at constant rate (the percentage of active ingredient released by the microbeads in one hour) and the latent period can be deduced.

The results obtained are shown in the table below:

| Test sample corresponding to 120 mg of active ingredient | Latent period | Rate of release per hour |
| --- | --- | --- |
| Sample A | 0 | 25% |
| Sample B | 2 hours | 13.75% |
| Sample C | 4 hours | 9% |

In this case, it is observed that the microbeads B and C did not comply with the characteristics of the invention (latent period too long) and that the membrane was required to be thicker than that of the microbeads A (too rapid dissolution) and consequently the operating conditions have been modified in order to give rise to the microbeads according to the invention.

Microbeads have thus been prepared to give a dose of 120 mg of active ingredient in a capsule No. 1 with 250 microbeads per capsule; these microbeads contain 48% by weight of active ingredient, the inert grain represents 31% by weight of the microbead whereas the membrane represents 17.5% by weight of the microbead.

Starting from a representing 11% of the final weight of the microbead. microbeads have also been prepared to give a dose of 300 mg of active ingredient in a capsule No. 0, which contained 75% by weight of active ingredient; the membrane represents 11% by weight of the microbead.

In vitro, these microbeads show practically no latent period, the rate of release is constant and the amount of diltiazem released at the end of 4 hours is about 40% of the total quantity whereas it is about 60% at the end of 6 hours.

These properties are not altered after at least 18 months storage at ambient temperature and after 3 months storage at 40° C. or at 55° C.

I claim:

1. Sustained-release diltiazem microbeads each of which comprises (a) a core including an inert grain substrate coated with a layer of the active ingredient combined with a binder surrounded by (b) a microporous membrane consisting essentially of a film-forming polymer insoluble in aqueous medium, a plasticizing agent, representing from 10 to 30% by weight of said film-forming agent, and a filling material representing 35 to 75% by weight of said membrane, wherein, as determined in vitro at a pH of between 1.5 and 7, a diltiazem release rate of approximately 10% per hour for at least 6 hours is attained after a latent period of less than one hour.

2. Microbeads according to claim 1, wherein the active ingredient is a water soluble salt of diltiazem.

3. Microbeads according to claim 1, wherein the active ingredient is diltiazem hydrochloride.

4. Microbeads according to claim 1, wherein the film forming polymer is selected from polyacrylates, polymethacrylates and alkylcelluloses.

5. Microbeads according to claim 4, wherein the film forming polymer is ethylcellulose.

6. Microbeads according to claim 5, wherein the ethylcellulose has a viscosity between 10 and 50 mPa.s.

7. Microbeads according to claim 1, wherein the filling material is selected from talc, silica, metal silicates, kaolin, lactose, sucrose and metal oxides.

8. Microbeads according to claim 7, wherein the filling material is talc.

9. Microbeads according to claim 1, wherein the plasticizing agent is castor oil.

10. Microbeads according to claim 1, wherein the active ingredient is diltiazem hydrochloride, the film forming polymer is selected from polyacrylates, polymethacrylates and alkylcelluloses and the filling material is selected from talc, silica, metal silicates, kaolin, lactose, sucrose and metal oxides.

11. Microbeads according to claim 1, wherein the active ingredient is diltiazem hydrochloride, the film forming polymer is ethylcellulose and the filling material is talc.

12. Microbeads according to claim 1, wherein the membrane consists of 25 to 40% by weight of ethylcellulose, from 5 to 10% by weight of castor oil and from 50 to 70% by weight of talc.

13. Microbeads according to claim 1, wherein the binder is polyvinyl pyrrolidone.

14. Microbeads according to claim 1, having a diameter from 0.4 to 1.4 mm, wherein the active ingredient is diltiazem hydrochloride, and wherein the membrane has a thickness of from 15 micrometers to 60 micrometers and consists essentially of 25 to 40% by weight of ethylcellulose, from 5 to 10% by weight of plasticizing agent and from 50 to 70% by weight of talc.

15. A process for the preparation of the microbeads according to claim 1, wherein the membrane is applied to the core by the spraying of a dispersion of its components in a solvent.

16. A sustained-release pharmaceutical composition of diltiazem, consisting essentially of capsules containing microbeads according to claim 1.

17. A pharmaceutical composition according to claim 16, wherein the capsule contains from 100 to 600 microbeads.

18. A pharmaceutical composition according to claim 17, wherein the capsule contains from 90 to 350 mg of diltiazem.

* * * * *